United States Patent [19]

Lezdey John et al.

[11] Patent Number: 5,134,119
[45] Date of Patent: Jul. 28, 1992

[54] TREATMENT OF INFLAMMATION USING 358 SUBSTITUTED ALPHA-ANTITRYPSIN

[76] Inventors: Lezdey John, 976 Kingston Dr., Cherry Hill, N.J. 08034; Allen Wachter, 9822 South Grandview, Tempe, Ariz. 85284

[21] Appl. No.: 643,910

[22] Filed: Jan. 18, 1991

Related U.S. Application Data

[63] Continuation-in-part of Ser. No. 598,241, Oct. 16, 1990.

[51] Int. Cl.$^5$ .................. A61K 37/64; C07K 15/14
[52] U.S. Cl. ............................ 514/8; 530/392; 514/12; 514/21; 514/2
[58] Field of Search ............ 530/392, 350; 514/8, 514/12, 21

[56] References Cited

U.S. PATENT DOCUMENTS

| | | | |
|---|---|---|---|
| 4,008,242 | 4/1991 | Lezdey et al. | 514/8 |
| 4,656,254 | 4/1987 | Shearer et al. | 530/392 |
| 4,732,973 | 3/1988 | Barr et al. | 530/350 |
| 4,734,279 | 3/1988 | Stephan et al. | 514/8 |
| 4,916,117 | 4/1990 | Lezdey et al. | 514/8 |

OTHER PUBLICATIONS

Allergy Proc. "The Mast Cell: a comprehensive Update Review" Bernstein et al, Sep.-Oct. 1990, vol. 11, No. 5, pp. 209-223.

Pannuculitis Associated with Severe 1-Antitrypsin Deficiency-Med. Affairs Arch Dermatol vol. 123, Dec. 1987.

Kevin C. Smith et al. Sequence Homology Between Human 1-Antichymotrypsin 1-Antitrypsin and Antithrombin III-Amer. Chem. Soc. vol. 22-No. 22 1983-T. Chandra et al.

Structure, Function, and Control of Neutrophil Proteinases-The American Journal of Medicine-vol. 84-Travis et al pp. 37-42.

J. Amer. Acad. of Dermatology, "The Mast Cell in Health & Disease" Rothe et al, vol. 23, No. 4, Part 1, pp. 615-624, Oct. 1990.

Biochem. Efficacy & Safety of Monthly Augmentation Therapy for Alpha$_1$-Antitrypsin Deficiency-Hubbard et al.-Jama, Sep. 2, 1988-vol. 260, No. 9-The Journal of Investigative Dermatology-Mar. 1991-vol. 96 No. 3.

*Primary Examiner*—Howard E. Schain
*Attorney, Agent, or Firm*—John Lezdey

[57] ABSTRACT

A method for the prophylaxis or direct treatment of mast cell implicated skin inflammation in a patient which comprises topically administering an effective amount of an analog of alpha 1-antitrypsin, its salts or derivatives, and compositions thereof.

9 Claims, No Drawings

TREATMENT OF INFLAMMATION USING 358 SUBSTITUTED ALPHA-ANTITRYPSIN

RELATED APPLICATIONS

This application is a continuation-in-part of application Ser. No. 598,241 filed Oct. 16, 1990, entitled "Treatment of Inflammation" of Lezdey et al.

FIELD OF THE INVENTION

The present invention relates to a method and composition for treating mammals afflicted with a certain mast cell implicated inflammatory disease. More particularly, the present invention relates to the direct or prophylaxis treatment of certain mast cell implicated inflammatory conditions in patients by administering the analogs of alpha 1-antitrypsin, their salts or derivatives thereof. There is particularly provided topical compositions for treating the symptoms of inflammatory skin conditions.

BACKGROUND OF THE INVENTION

Inflammation leading to tissue damage is regulated by numerous phlogistic mediators. Since eosinophils, neutrophils, basophils, lymphocytes and mast cells contain large numbers and amounts of proteases, they appear to be implicated both in the regulation of inflammation and in the damage incurred during inflammation. Essentially any connective tissue can be degraded by one or more proteases.

Human neutrophils utilize a variety of destructive enzymes during the process of phagocytosis. The major enzymes have been determined to be elastase, cathepsin G, myeloperoxidase and lysozyme.

It has now been found that controlling the amount of the destructive enzymes at the site of inflammation can prevent proliferation of the disease, prevent associated tissue damage and promote healing. It has also been found that the administration of alpha 1-antitrypsin alone provides a major control of the symptoms of the disease or burns. However, since the cause of disease may be a result of more than one factors, the use of more than one protease inhibitor provides a better chance of success for early remission of the symptoms and for a prophylactic control of the symptoms associated with the disease. Alpha 1-antitrypsin when administered with other serine protease inhibitors, for example, alpha 2-macroglobulin, alpha 1-antichymotrypsin and C-reactive protein (CRP), provides a reduction in swelling, pain and stiffness.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Alpha 2-macroglobulin is a glycoprotein containing 8–11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha 1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Inhibitors. 1st, 1–21 (1970).

U.S. Pat. No. 4,916,117 to Lezdey et al discloses the treatment of pulmonary inflammation with microcrystalline alpha-1-antichymotrypsin.

U.S. Pat. No. 4,732,973 to Barr et al, which is herein incorporated by reference, discloses the preparation of the analogs of human-1-antitrypsin wherein the amino acid corresponding to the methionine at position 358 of wild-types alpha-1-antitrypsin is substituted with an aliphatic amino acid.

SUMMARY OF THE INVENTION

The present invention relates to a method for treating mast cell implicated inflammatory skin conditions in patients by the topical administration of the analogs alpha 1-antitrypsin or derivatives thereof alone or in combination with one or more other serine protease inhibitors in a suitable pharmaceutical composition.

The analogs of alpha 1-antitrypsin ($\alpha_1$-PI) has been especially useful in the treatment of the various inflammatory skin conditions including those which are induced by autoimmune disease, virus and bacterial infections. The compositions have also been found to cause vasoconstriction, which in inflammation, decreases swelling and redness and to eliminate pain and itching. This feature is especially useful in burns.

Atopic dermatitis is characterized by pruritis, asteatosis, lichenification and weeping wounds that undergo periods of exacerbations and remissions. Current therapy is mainly symptomatic and consists of both oral and topical steroids, antipruritics, coal tar preparations, U.V. light and food avoidance. Steroids are the mainstay of therapy. Unfortunately, steroids produce many undesirable side effects which include skin atrophy, telangiectasia, purpura, striae and when applied to large areas of the body they suppress the hypothalamic-pituitary-adrenal axis. $\alpha_1$-PI (Alpha$_1$-Proteinase Inhibitor) was used as an alternative to steroids for the treatment of atopic dermatitis.

Multiple immunologic abnormalities have been documented in atopic dermatitis, namely, (1) Defective cellular immunity with anergy to recall antigens, (2) Quantitative T-cell suppressor deficiency, (3) Decreased lymphocyte blast cell transformation after PHA (phytohemagglutin) exposure, (4) Decreased polymorphonuclear and monocyte chemotaxis, (5) Elevated serum IgE levels and (6) Mast cells and their mediators have been identified as having a significant causative role.

Mast cells play a critical role in inflammation by linking both the humoral and cellular immune systems. Both IgE and non-IgE mechanisms activate mast cells to degranulate their mediators which are chemoactive for eosinophils and neutrophils. This pattern is a common denominator in many diseases such as atopic dermatitis, asthma, allergic rhinitis and other inflammatory diseases.

The analogs of $\alpha$,-PI of the present invention have as their target, elastase, as well as other serine proteases. The analogs of $\alpha_1$-PI also have an affinity to cathepsin-G which is a mediator of neutrophils, and human mast cell chymase which is a mediator of skin mast cells. It is believed that atopic dermatitis is an example of uncontrolled tissue inflammation mediated by mast cells and neutrophils. The present analogs of $\alpha$,-PI are safe and beneficial in the management of chronic atopic dermatitis as well as contact dermatitis.

The analogs used in the subject invention may be glycosylated or non-glycosylated, preferably non-glycosylated and are available using hybrid constructs involving combining DNA sequences from diverse sources. Hybrid polypeptides similar to the wild type may be prepared which will generally range from about 350 to 500 amino acids. These polypeptides will, except for the modification of the methionine residue retain the $\alpha_1$-antitrypsin sequence for all oligopeptide sequence of at least about 10 amino acids, usually at least about 40 amino acids, and more usually at least 80 amino acids, which sequence includes the active site of $\alpha_1$-antitrypsin and at least five amino acids flanking both sides of the active site. Where using the numbering of $\alpha_1$-antitrypsin, this will involve amino acids 290 to 394, more particularly, 310 to 390 and preferably 340 to 380.

The substitution of from four to five carbon atoms, where the side chain may be hydrocarbon or hydroxy substituted hydrocarbon, preferably hydrocarbon, including alanine, valine, leucine, isoleucine, serine, and threonine, particularly leucine.

The leucine analog of $\alpha_1$-antitrypsin is particularly advantageous since it is believed to have an affinity to tryptase containing mast cells. Such affinity is not found with $\alpha_1$-antitrypsin.

The salts and derivatives of the analogs of the invention may be formed utilizing conventional techniques associated with other proteins without effecting the utility of the compound. There may be prepared the alkali metal salts, acid-addition salts, and esters similar to other proteins or peptides.

Some inflammation conditions are not immediately identifiable as to source and the factors which are involved to produce the different symptoms are not readily apparent. Therefore, it is desirable to administer in some case a combination or cocktail of serine protease inhibitors to provide a broad spectrum of drugs which can provide rapid relief of the different symptoms of inflammation. The most effective combination is alpha 1-antichymotrypsin and the analog of alpha 1-antitrypsin and optionally alpha 2-macroglobulin. Preferably, the combination is administered in a ratio of 1:1:1: to 3:2:1: either in a single unit or in separate dosage form.

When topically applied, the analog of alpha 1-antitrypsin in suitable composition form are useful in the treatment of burns and mast cell implicated inflammatory skin diseases which include psoriasis, eczema, acne, and the like. Similar to treatment with alpha 1-antitrypsin, the analogs of the invention also reduce pain when applied to skin lesions. Preferably, the compositions of the invention are administered to patients showing an increased IgE level through the use of a patch test or serum analysis. That is, the patient shows an allergic condition.

It is therefore an object of the invention to provide an anti-inflammatory composition containing the analogs of $\alpha_1$-antitrypsin which can relieve the swelling and redness associated with mast cell implicated inflammatory conditions.

It is a further object of the invention to provide an anti-inflammatory composition which is well tolerated by the human body and is free of side effects.

It is a yet still further object of the invention to provide a method and a composition for treating mast cell implicated inflammatory skin conditions.

DETAILED DESCRIPTION OF THE PRESENT INVENTION

The objects of the present invention can be achieved by the administration of the analogs of alpha 1-antitrypsin wherein the amino acid corresponding to the methionine position 358 of wild-type $\alpha_1$-antitrypsin is substituted with an aliphatic amino acid. The analog may be administered alone or in combination with other serine protease inhibitors in suitable pharmaceutical form to patients suffering from inflammatory skin conditions which includes burns.

The present invention provides a pharmaceutical composition which comprises the compound of this invention and a pharmaceutically acceptable carrier.

In the treatment of burns, a 10–20% solution of the analogs of $\alpha$ 1-antitrypsin are used, alone or in combination with other serine protease inhibitors and growth factors, in sterile water or saline solution, that may be applied to the site of injury or the burn area may be wrapped in wet bandages. The treatment provides immediate relief of pain. The patient may then be treated with the solution daily until the healing proceeds normally. Depending upon the severity of the burns, the patient may be further treated with other medications to prevent infection.

The following examples further illustrate the practice of this invention, but are not intended to be limiting thereof. It will be appreciated that the selection of actual amounts of specific drug to be administered to any individual patient (human or animal) will fall within the discretion of the attending physician and will be prescribed in a manner commensurate with the appropriate dosages will depend on the stage of the disease and like factors uniquely within the purview of the attending physician.

EXAMPLE I

A topical cream was prepared as follows:

| A. The following mixture was prepared: | |
|---|---|
| The leucine analog of $\alpha$ 1-antitrypsin | 1.0 g |
| Olive oil | 5.0 g |
| Cetanol | 2.0 g |
| Stearic acid | 5.0 g |
| Glycerin aliphatic acid ester | 12.0 g |
| Tween 60 | 0.5 g |
| B. The following mixture was also prepared: | |
| Propylene glycol | 0.5 g |
| Methyl paraben | 0.1 g |
| Propyl paraben | 0.02 g |
| Purified water | to 100 g in total |

The mixture of parts A and B were blended together by conventional means to give a total of 100 g. of 100% by weight topical cream which could be utilized for treatment of acne, eczema, psoriasis, or other inflammatory dermatological conditions. If desired alpha 2-macroglobuli or $\alpha_1$-antichymotrypsin may be added in an amount of 1.0 g to part A.

EXAMPLE II

An oleogenous anhydrous ointment was prepared with the following composition:

| Composition | % |
| --- | --- |
| The valine analog of α 1-antitrypsin | 1.0 |
| Soy phosphatide | 4.0 |
| Plastibase 50W | 94.975 |
| Butylated hydroxytoluene | 0.025 |
| | 100.00 |

If desired, in lieu of the valine analog of alpha 1-antitrypsin as the active principal, there may utilized the alanine leucine isoleucine, serine or threonine analog of alpha 1-antitrypsin. Other non-aqueous lipid miscible carriers may also be utilized.

EXAMPLE III 1000 mg of the leucine analog of $\alpha$1-antitrypsin was dissolved in 50 ml of saline solution. A patient suffering from atopic dermatitis with swelling and open lesions of the hand was treated by immersing the hand in the solution. Treatment was continued for 1 hour and the swelling was reduced.

EXAMPLE IV

A suitable cream for topical use was prepared by admixing 43 g of the valine analog of $\alpha_1$-antitrypsin with 6 ml of water and 1000 g of a balm available under the trademark AQUAPHOR, sold by Beiesdorf Inc., Norwalk, Conn. AQUAPHOR comprises a mixture of petrolatum, mineral oil, wax and wool wax alcohol.

The cream is useful for minor irritations and in the prophylaxis treatment of inflammatory skin conditions.

I claim:

1. A method for the treatment of mast cell implicated inflammation of the skin in a patient which comprises topically administering an effective amount of an analog of alpha 1- antitrypsin wherein the amino acid corresponding to the methionine at position 358 is substituted with an aliphatic amino acid, its salt or derivative, to the site of inflammation so as to control the amount of elastase and cathepsin G.

2. The method of claim 1 wherein said alpha 1-antitrypsin is recombinant.

3. The method of claim 1 wherein said skin inflammation is a result of dermatitis or psoriasis.

4. The method of claim 3 wherein said skin inflammation is a result of atopic dermatitis.

5. The method of claim 1 wherein said aliphatic amino acid is selected form the group consisting of alanine, valine, leucine, isoleucine, serine and threonine.

6. The method of claim 7 wherein said aliphatic amino acid is leucine.

7. The method of claim 1 wherein said patient has an increase in IgE level.

8. A method for treating the symptoms of burns in a patient which comprises topically administering an effective amount of an analog of alpha 1-antitrypsin wherein the amino acid corresponding to the methionine at position 358 is substituted with an aliphatic amino acid, the derivatives or salts thereof, to said patient at the site of the burn so as to control the amount of elastase and cathepsin G.

9. The method of claim 8 wherein said analog is of a recombinant alpha 1-antitrypsin.

* * * * *